United States Patent
Lian et al.

(10) Patent No.: US 11,388,917 B2
(45) Date of Patent: Jul. 19, 2022

(54) METHOD FOR REMOVING BENZO[A]PYRENE FROM LIPOSOLUBLE NATURAL EXTRACT

(71) Applicant: Chenguang Biotech Group, Co. Ltd., Handan (CN)

(72) Inventors: Yunhe Lian, Handan (CN); Wei Gao, Handan (CN); Yuanxin Cheng, Handan (CN); Xiangyu Yang, Handan (CN); Xiaodong An, Handan (CN); Zhipeng Duan, Handan (CN); Zhiming Zhang, Handan (CN)

(73) Assignee: Chenguang Biotech Group, Co., Ltd.

( * ) Notice: Subject to any disclaimer, the term of this patent is extended or adjusted under 35 U.S.C. 154(b) by 557 days.

(21) Appl. No.: 15/777,755

(22) PCT Filed: Nov. 1, 2016

(86) PCT No.: PCT/CN2016/104223
§ 371 (c)(1),
(2) Date: May 21, 2018

(87) PCT Pub. No.: WO2017/084493
PCT Pub. Date: May 26, 2017

(65) Prior Publication Data
US 2018/0338513 A1    Nov. 29, 2018

(30) Foreign Application Priority Data
Nov. 19, 2015    (CN) .......................... 201510801297.6

(51) Int. Cl.
| | | |
|---|---|---|
| A23L 5/20 | (2016.01) | |
| C07C 11/21 | (2006.01) | |
| A23L 5/40 | (2016.01) | |
| C09B 61/00 | (2006.01) | |
| C07C 403/24 | (2006.01) | |
| C07C 7/00 | (2006.01) | |
| B01D 21/26 | (2006.01) | |

(52) U.S. Cl.
CPC .................. *A23L 5/23* (2016.08); *A23L 5/40* (2016.08); *B01D 21/262* (2013.01); *C07C 7/00* (2013.01); *C07C 11/21* (2013.01); *C07C 403/24* (2013.01); *C09B 61/00* (2013.01); *A23V 2002/00* (2013.01)

(58) Field of Classification Search
CPC . C07C 7/00; C07C 11/21; C09B 61/00; A23L 5/23; B01D 21/262; A23V 2002/00
See application file for complete search history.

(56) References Cited

U.S. PATENT DOCUMENTS 5,965,183 A * 10/1999 Hartal ...................... A23L 5/44
426/250

FOREIGN PATENT DOCUMENTS

| CN | 1384714 A | 12/2002 | |
|---|---|---|---|
| CN | 101455708 A | 6/2009 | |
| CN | 101455708 B * | 4/2011 | |
| CN | 105481745 A | 4/2016 | |
| WO | WO-9748287 A1 * | 12/1997 | ............. A23L 19/09 |
| WO | WO-2013041935 A1 * | 3/2013 | ............. A61K 31/01 |

OTHER PUBLICATIONS

Handa et al., "Extraction Technologies for Medicinal and aromatic plants". from 'Italian Ministry of Foreign Affairs', pp. 22-45. (Year: 2008).*
Tepe et al., "Antimicrobial and antioxidant activities of the essential oil and various extracts of *Salvia tomentosa* Miller (Lamiaceae)". Food Chemistry 90 (2005)333-340. (Year: 2005).*
"Chemistry 210 Experiment Ib". Available online at https://home.miracosta.edu/dlr/210exp1b.htm (Year: 2012).*
"Toxicological Review of Benzo[a]pyrene". Available online at https://iris.epa.gov/static/pdfs/0136tr.pdf on Jan. 2017 (Year: 2017).*
International Search Report; dated Jan. 18, 2017 for PCT Application No. PCT/CN2016/104223.

* cited by examiner

*Primary Examiner* — Erik Kashnikow
*Assistant Examiner* — Assaf Zilbering
(74) *Attorney, Agent, or Firm* — Mendelsohn Dunleavy P.C.

(57) ABSTRACT

Disclosed is a method for removing benzo[α]pyrene from a liposoluble natural extract. The method of the present invention comprises adding a suitable solvent to a crude natural extract product so as to obtain a mixed material; heating the mixed material, stirring until uniform, cooling and layering, and then separating the upper layer from the lower layer so as to obtain a precipitate and a filtrate; washing the precipitate with a small amount of a solvent so as to obtain a washed product and a washing solution; removing the solvent from the washed product at a low temperature so as to obtain a finished product; and directly recycling the filtrate and the washing solution as solvents. The present method achieves the purification of the crude natural extract product and the removal of benzo[α]pyrene in one step, and is a novel method which is simple, highly efficient, feasible and easy for industrial applications.

9 Claims, No Drawings

METHOD FOR REMOVING BENZO[A]PYRENE FROM LIPOSOLUBLE NATURAL EXTRACT

TECHNICAL FIELD

The present invention belongs to the technical field of natural plant extracts, in particular relates to a method for removing benzo[α]pyrene from a liposoluble natural extract.

BACKGROUND ART

Benzo[α]pyrene is a kind of polycyclic aromatic hydrocarbons with strong carcinogenicity. Benzo[α]pyrene has stable chemical properties at room temperature, and mainly exists in flue gas from the combustion of coal tar, various types of carbon black, coal and petroleum; smoke from cigarette; and automobile exhaust, as well as industrial wastewater from cooking, oil refining, asphalt, plastics and the like, and is also easily produced in foods cooked under a high temperature. Due to the increasing numbers of automobiles and the high levels of the discharge of industrial wastewater and exhaust gas, the amount of benzo[α]pyrene contamination in air, water, and soil has gradually increased, and natural plants that rely on air, water, and soil are also inevitably contaminated by benzo[α]pyrene.

Capsanthin, lutein and lycopene extracted from natural plants are all new functional natural pigments with health care activity, and are popular with consumers for their strong natural biological activities. With the increasing demands for natural extracts, people's demand for product safety is increasing. Studies have found that, some liposoluble natural extracts produced at home and abroad contain a trace or small amount of benzo[α]pyrene, which results in certain risks. Therefore, under the severe situation of food safety, it is necessary to develop a method for removing benzo[α]pyrene from a natural extract.

At present, most of the methods for removing benzo[α]pyrene from edible oils are adsorption with activated carbon, ultraviolet light degradation, or high temperature distillation and some other methods, and several method for reducing benzo[α]pyrene contamination in the environment are lactobacillus adsorption, oxidation by strong oxidant, combustion and other methods. However, the methods for removing benzo[α]pyrene from a natural extract have not been reported. The natural extract itself is easily adsorbed by activated carbon, very sensitive to light, high temperature and oxidant, and easily oxidized to fade and degenerate, and thus, the direct use of the above methods for removing benzo[α]pyrene results in serious loss of active ingredients. Therefore, it is very important to specifically develop a method for removing benzo[α]pyrene from a natural extract based on the characteristics of the natural extract.

SUMMARY OF THE INVENTION

In order to overcome the shortcomings in the prior art, the present invention provides a method for removing benzo[α]pyrene from a liposoluble natural extract. The method is simple in operation, easy to realize industrialization, can decrease the loss of effective components and can effectively remove benzo[α]pyrene from a liposoluble natural extract.

In order to solve the above technical problems, the technical solution adopted by the present invention is a method for removing benzo[α]pyrene from a liposoluble natural extract, comprising the following steps:

(1) adding a solvent to a crude natural extract product so as to obtain a mixed material;

(2) heating the mixed material, stirring until uniform, cooling and layering, and then separating the upper layer from the lower layer so as to obtain a precipitate and a filtrate;

(3) washing the precipitate with a solvent so as to obtain a washed product and a washing solution; and (4) removing the solvent from the washed product at a low temperature so as to obtain a finished product; directly recycling the filtrate in step (2) and the washing solution in step (3) as solvents.

The crude natural extract product in step (1) of the present invention is a liposoluble natural extract.

The crude natural extract product in step (1) of the present invention is any one selected from the group consisting of lycopene oleoresin, lutein extract saponifiable matters and capsanthin semi-finished products.

The solvent in step (1) of the present invention is any one or more selected from the group consisting of ethyl acetate, n-hexane, cyclohexane, solvent-extracted oil No. 6, methanol, ethanol and acetone; and the filtrate in step (2) and the washing solution in step (3) may also be selected as a solvent.

In step (1) of the present invention, the mass-volume ratio of the crude natural extract product to the solvent is 1:(2.5 to 5), wherein the unit of mass of the crude natural extract product is kg, and the unit of volume of the solvent is L.

In step (2) of the present invention, the heating temperature is 35 to 65° C.

In step (2) of the present invention, the cooling manner is cooling to room temperature by cooling water or natural cooling.

In step (2) of the present invention, the manner for separating the materials is centrifugal separation or filtering separation; the filtration manner is a plate-and-frame filtration or vacuum filtration; and the pore size of the filter cloth is 300 to 1000 mesh.

The method according to the present invention is applicable to crude natural extract products in any form. However, the difficulty level for separating benzo[α]pyrene form crude natural extract products in different forms are different. For example, for powdered crude natural extract products, benzo[α]pyrene can be easily separated, and step (2) can be performed only once, but for crude natural extract paste products or other crude natural extract products in which benzo[α]pyrene can be easily encapsulated, it is necessary to repeat step (2), until the content of benzo[α]pyrene in the precipitate is less than 2 μg/kg, and then the next step can be performed.

The solvent used in step (3) of the present invention is any one or more selected from the group consisting of ethyl acetate, acetone, n-hexane and cyclohexane; the solid-liquid ratio is 2:1 to 4:1. Wherein, the solvent used in step (3) and the solvent used in step (1) may be the same or different, but the solvent used in step (3) must be a fresh solvent.

The design idea of the present invention is that the substance of the crude natural extract product is complex and viscous, and is easily dissolved and dispersed in a heated solvent, which is favorable for dispersing and releasing the encapsulated benzo[α]pyrene and active ingredients.

Benzo[α]pyrene is soluble in ethyl acetate, methanol, ethanol, acetone, n-hexane and cyclohexane, and a trace amount of benzo[α]pyrene does not precipitate after the system is cooled. However, a liposoluble natural extract can be dissolved in the above hot solvents, but the solubility thereof varies greatly at different temperatures, and after the system is cooled, the extract will be largely precipitated or layered. Therefore, benzo[α]pyrene can be removed together with other matrix impurities by separation after cooling, and the product can be further washed with a small amount of a benign solvent to give a natural extract containing almost no benzo[α]pyrene. The small amount of active ingredients dissolved in the filtrate and the washing solution are recovered together with the solvents and put into a new round of production, so as to reduce the losses and save costs.

The beneficial effects produced by adopting the above technical solution lie in that: the present invention performs by utilizing the difference in solubility between benzo[α]pyrene and the active ingredients of a natural extract, and has a good treatment effect and a high yield for the product; the purification of the crude natural extract product and the removal of benzo[α]pyrene can be achived in one step, which saves time and efforts. The solvent used for treating the product can be recycled, which saves cost and reduces pollution discharge and waste. The entire process has a high degree of automation, is simple and rapid, and can obtain a natural extract product with a content of benzo[α]pyrene less than 10 μg/kg in one step, which is easy to realize industrial production.

SPECIFIC MODES FOR CARRYING OUT THE EMBODIMENTS

The following describes the present invention in further detail with reference to specific Examples.

Example 1

(1) 300 kg of lycopene oleoresin was added into a deodorization pot, benzo[α]pyrene was artificially added so as to achieve a content of 30 μg/kg, 1000 L of mixed solvent in which the volume ratio of ethyl acetate to ethanol with 1:1 was added, and the pot was covered;

(2) the materials were heated to 40° C., stirred well, and cooled to room temperature by cooling water, and then layered;

(3) the materials were pumped into a plate-and-frame filter by a vacuum pump, and the filtrate was recovered;

(4) 120 L of low-temperature ethyl acetate was pumped into the plate-and-frame filter with a 300 mesh filter cloth, the lycopene crystals on the plate and frame was washed and a nitrogen gas was introduced until the materials were half dried; and the washing solution was recovered;

(5) the lycopene crystals on the plate and frame were removed and vacuum dried at a low temperature; the weight yield was 89%, and using a method according to "GBT22509-2008 Determination of benzo[α]pyrene in animal and vegetable oils by reversed phase high-performance liquid chromatography", the content of benzo[α]pyrene was less than 2 μg/kg, which can be used to blend products; and (6) the recovered filtrate and washing solution were used as a solvent for the treatment of lycopene oleoresin in the next pot, but a fresh solvent must be used in step (4).

Example 2

(1) 150 kg of lutein extract saponifiable matters was added to a stirring pot, benzo[α]pyrene was artificially added so as to achieve a content of 60 μg/kg, and 450 L of n-hexane was added, and the pot was covered;

(2) the materials were heated to 45° C., stirred, and cooled to room temperature by colling water and then layered;

(3) the materials were pumped into a plate-and-frame filter by a vacuum pump, and the filtrate was recovered;

(4) 70 L of low-temperature acetone was pumped into the plate-and-frame filter with a 1000 mesh filter cloth, the lutein crystals on the plate and frame were washed, and a nitrogen gas was introduced until the materials were half dried; and the washing solution was recovered;

(5) the lutein crystals on the plate and frame were removed and vacuum dried at room temperature; the weight yield was 80%, and using a method according to "GBT22509-2008 Determination of benzo[α]pyrene in animal and vegetable oils by reversed phase high-performance liquid chromatography", the content of benzo[α]pyrene was less than 2 μg/kg, which can be used to blend products; and (6) the recovered filtrate and washing solution were used as a solvent for the treatment of lutein extract saponifiable matters in the next pot, but a fresh solvent must be used in step (4).

Example 3

(1) 150 kg of lutein extract saponifiable matters was added to a stirring pot, benzo[α]pyrene was artificially added so as to achieve a content of 30 μg/kg, and 750 L of n-hexane was added, and the pot was covered;

(2) the materials were heated to 65° C., stirred well, cooled to room temperature by colling water, and then layered;

(3) the materials were pumped into a plate-and-frame filter by a vacuum pump, and the filtrate was recovered;

(4) 70 L of low-temperature acetone was pumped into the plate-and-frame filter with a 500 mesh filter cloth, the lutein crystals on the plate and frame were washed, and a nitrogen gas was introduced until the materials were half dried; and the washing solution was recovered;

(5) the lutein crystals on the plate and frame were removed and vacuum dried at room temperature; the weight yield was 82%, and using a method according to "GBT22509-2008 Determination of benzo[α]pyrene in animal and vegetable oils by reversed phase high-performance liquid chromatography", the content of benzo[α]pyrene was less than 2 μg/kg, which can be used to blend products; and (6) the recovered filtrate and washing solution were used as a solvent for the treatment of lutein extract saponifiable matters in the next pot, but a fresh solvent must be used in step (4).

Example 4

(1) 120 kg of capsanthin semi-finished product was added to a stirring pot, benzo[α]pyrene was artificially added so as to achieve a content of 48 μg/kg, and 300 L of methanol was added, and the pot was covered.

(2) the materials were heated to 35° C., stirred and naturally cooled to room temperature by standing, and the upper layer was separated from the lower layer by centrifugation;

(3) repeating the above operation once;

(4) 40 L of low-temperature n-hexane was used to wash the capsanthin separated by centrifugation, and then centrifugation was preformed again; and the washing solution was recovered;

(5) the washed capsanthin was subjected to the removal of solvent residues in vacuum in a deodorization pot at 50° C., the weight yield was 96%, and using a method according to "GBT22509-2008 Determination of benzo[α]pyrene in animal and vegetable oils by reversed phase high-performance liquid chromatography", the content of benzo[α]pyrene was less than 2 μg/kg, which can be used to blend products;

(6) the recovered washing solution was used as a solvent for the treatment of capsanthin semi-finished product in the next pot, but a fresh solvent must be used in step (4).

The above Examples merely describe the preferred embodiments of the present invention, and do not limit the scope of the present invention. Without departing from the spirit of the present invention, various modifications and improvements made by a person skilled in the art to the technical solutions of the present invention should fall within the scope of the protection defined by the claims of the present invention.

INDUSTRIAL APPLICABILITY

The present invention provides a method for removing benzo[α]pyrene from a liposoluble natural extract, which has a good product treatment effect and a high yield. The purification of the crude natural extract product and the removal of benzo[α]pyrene can be achived in one step, which saves time and efforts. The solvent used for treating the product can be recycled, which saves cost and reduces pollution discharge and waste. The entire process has a high degree of automation, is simple and rapid, and can give a natural extract product with a content of benzo[α]pyrene less than 10 μg/kg in one step, and moreover, the process is easy to realize industrial production.

What is claimed is:

1. A method for removing benzo[α]pyrene from a liposoluble natural extract that contains lycopene and benzo[α]pyrene, characterized in that, the method comprises the following steps:
    (1) adding a solvent to a crude natural extract product so as to obtain a mixed material;
    (2) heating the mixed material and stirring until uniform to dissolve the crude natural extract product, essentially all of the lycopene and the benzo[α]pyrene in the solvent, cooling to form an upper layer and a lower layer in the mixture by crystallization of the lycopene from the solvent, and then separating the upper layer from the lower layer so as to obtain a precipitate containing crystallized lycopene and a filtrate containing benzo[α]pyrene;
    (3) washing the precipitate with a solvent so as to obtain a washed product and a washing solution; and
    (4) removing the solvent from the washed product at a low temperature so as to obtain a finished product;
    wherein the filtrate in step (2) and the washing solution in step (3) are directly recycled as solvents;
    the crude natural extract product in step (1) is any one selected from the group consisting of lycopene oleoresin, lutein extract saponifiable matters and capsanthin semi-finished products; and
    the solvent in step (1) is any one or more selected from the group consisting of ethyl acetate, n-hexane, cyclohexane, solvent-extracted oil No. 6, methanol, ethanol and acetone.

2. The method for removing benzo[α]pyrene from a liposoluble natural extract according to claim 1, characterized in that, the mass-volume ratio of the crude natural extract product to the solvent in step (1) is from 1:2.5 to 1:5, wherein the unit of mass of the crude natural extract product is kg, and the unit of volume of the solvent is L.

3. The method for removing benzo[α]pyrene from a liposoluble natural extract according to claim 1, characterized in that, the heating temperature in step (2) is 35 to 65° C.

4. The method for removing benzo[α]pyrene from a liposoluble natural extract according to claim 1, characterized in that, the cooling in step (2) is cooling to room temperature by cooling water or natural cooling.

5. The method for removing benzo[α]pyrene from a liposoluble natural extract according to claim 1, characterized in that, the manner for separating the materials in step (2) is centrifugal separation or filtering separation; the filtration is plate-and-frame filtration or vacuum filtration; and the pore size of a filter cloth is 300 to 1000 mesh.

6. The method for removing benzo[α]pyrene from a liposoluble natural extract according to claim 1, characterized in that, the solvent used in step (3) is any one or more selected from the group consisting of ethyl acetate, acetone, n-hexane and cyclohexane; and the solid-liquid ratio is 2:1 to 4:1.

7. The method for removing benzo[α]pyrene from a liposoluble natural extract according to claim 1, characterized in that, step (2) can be repeated.

8. The method for removing benzo[α]pyrene from a liposoluble natural extract according to claim 1, characterized in that, the manner for separating the materials in step (2) is centrifugal separation or filtering separation; the filtration is plate-and-frame filtration or vacuum filtration; and the pore size of a filter cloth is 300 to 500 mesh.

9. A method for removing benzo[α]pyrene from a liposoluble natural extract that contains lycopene and benzo[α]pyrene, characterized in that, the method comprises the following steps:
    (1) adding a solvent to a crude natural extract product so as to obtain a mixed material;
    (2) heating the mixed material and stirring until uniform, cooling to form an upper layer and a lower layer, and then separating the upper layer from the lower layer so as to obtain a precipitate and a filtrate;
    (3) washing the precipitate with a solvent so as to obtain a washed product and a washing solution; and
    (4) removing the solvent from the washed product at a low temperature so as to obtain a finished product;
    wherein the crude natural extract product in step (1) is any one selected from the group consisting of lycopene oleoresin, lutein extract saponifiable matters and capsanthin semi-finished products;
    the mass-volume ratio of the crude natural extract product to the solvent in step (1) is from 1:2.5 to 1:5, wherein the unit of mass of the crude natural extract product is kg, and the unit of volume of the solvent is L; and
    the solvent in step (1) is any one or more selected from the group consisting of ethyl acetate, n-hexane, cyclohexane, solvent-extracted oil No. 6, methanol, ethanol and acetone.

* * * * *